US00PP33133P2

(12) United States Plant Patent
Horvath

(10) Patent No.: US PP33,133 P2
(45) Date of Patent: Jun. 1, 2021

(54) ***SALVIA NEMOROSA* PLANT NAMED 'SIXTEEN CANDLES'**

(50) Latin Name: *Salvia nemorosa*
Varietal Denomination: Sixteen Candles

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/974,171

(22) Filed: Nov. 2, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Susan McCormick Ewoldt

(57) ABSTRACT

A new, distinct *Salvia nemorosa* plant as shown and described, characterized by the combination of purple stems, deep pink flowers, and purple calyxes compared to the seed parent.

1 Drawing Sheet

Latin name: *Salvia nemorosa.*
Cultivar name: 'Sixteen Candles'.

BACKGROUND OF THE INVENTION

The present invention relates to a new and distinct hybrid of *Salvia nemorosa* plant named 'Sixteen Candles' characterized by the combination of purple stems, deep pink flowers, and purple calyxes compared to the seed parent. The new *Salvia nemorosa* was raised as a seedling from open pollinated seed sown from the seed parent *Salvia nemorosa* 'Caradonna', not patented, in Hebron, Ill. in 2009. The selection of the new plant was due to its' mostly unbranched and upright purple stems, deep-pink flower spikes, and purple calyxes compared to the seed parent. Initial asexual reproduction has taken place at a nursery in Hebron, Ill. since 2014 by means of division, and vegetative cuttings. The new *Salvia nemorosa* has shown to be stable and identical in reproduction to the parent after rooting over 1000 plants from 2014 to 2019. No plants of the new *Salvia nemorosa* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Salvia nemorosa* plant named 'Sixteen Candles' characterized by mostly un-branched and upright purple stems, deep-pink flower spikes, and purple calyxes compared to the seed parent have been observed to be unique and stable. For purpose of comparison the new plant will be referred to as 'Sixteen Candles'.

Plants of 'Sixteen Candles' can be compared to the seed parent plant of *Salvia nemorosa* 'Caradonna', not patented. 1. The 'Sixteen Candles' plant is shorter growing to 33-36 cm while *Salvia nemorosa* 'Caradonna' grows to 60 cm. 2.

The 'Sixteen Candles' plant has a flower color of mostly N78 A, B & C while *Salvia nemorosa* 'Caradonna' has a flower color of N88 A.

Plants of 'Sixteen Candles' can also be compared to a pink flowered *Salvia nemorosa*, 'Pink Profusion' U.S. Pat. No. 31,435, patented. 1. The 'Sixteen Candles' plant is shorter growing to 33-36 cm while *Salvia nemorosa* 'Pink Profusion' grows to 41 cm. 2. The 'Sixteen Candles' plant has a flower color of N78 A,B & C while *Salvia nemorosa* 'Pink Profusion' has a flower color of 77A and 77B.

Plants of 'Sixteen Candles' can also be compared to another pink flowered *Salvia nemorosa,* 'Sensation Rose' U.S. Pat. No. 18,230, patented. 1. The 'Sixteen Candles' plant is taller growing to 33-36 cm while *Salvia nemorosa* 'Sensation Rose' grows to 27 cm. 2. The 'Sixteen Candles' plant has a flower color of N78 A,B & C while *Salvia nemorosa* 'Sensation Rose' has a flower color of 75 A.

DESCRIPTION OF PHOTOGRAPHS

Figure 1:
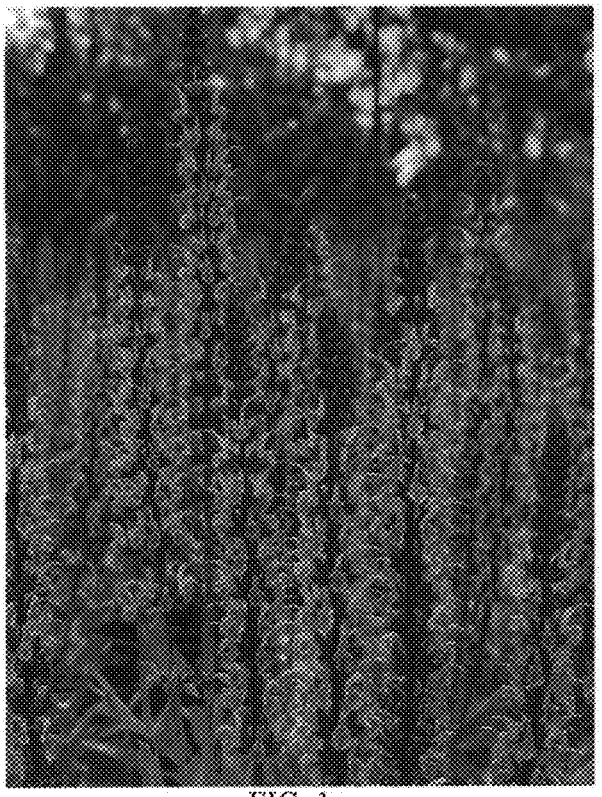
Figure 2:
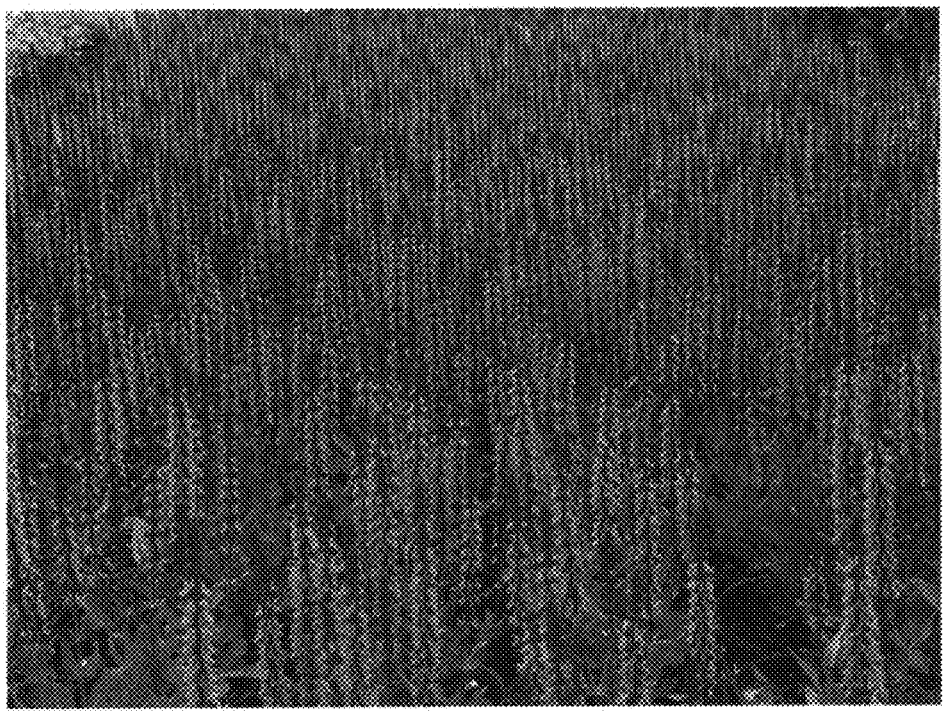

Plants pictured in the drawing were grown for two years.
FIG. 1. Close up of the flower stems.
FIG. 2. A group of potted plants.

DETAILED BOTANICAL DESCRIPTION

In the following description, color references are made to The Royal Horticultural Society Colour Chart (2001). Plants used for the description were grown for two years. Measurements and numerical values represent averages of typical plants.

PLANT

Botanical classification: *Salvia nemorosa* L.
Form: Globular shape.
Height: 33-36 cm from soil to top of flowers; 38 cm wide.
Growth: Herbaceous perennial, broad upright, moderate vigor.

*Roots*.—Fine, compact, dense, freely branching, white.

Stem:
- *Form.*—Quadrangular, strong.
- *Color.*—Yellow-green, close to at the base 145 A at the top half N77 C, being speckled and becoming more purple at the inflorescence with both colors at times.
- *Pubescence.*—Densely covered with short grayish white hairs, about 0.2 mm long, more so on the bottom half of the stem.

Branching:
- *Form.*—Branching from base, no pinching required.
- *Diameter.*—5 mm.
- *Length.*—36 cm.
- *Internode length.*—3-4 cm.
- *Quantity.*—About 40 flowering lateral branches.

Foliage:
- *Arrangement.*—Opposite.
- *Number of leaves per branch.*—22, 11 pairs.
- *Number of leaves per secondary branch.*—8-36 leaves, 4-18 pair.
- *Size of leaf.*—Length: 6 cm on average, shorter at tops of stems. Width: 2-3 cm.
- *Shape of leaf.*—Lanceolate.
- *Shape of tip.*—Acute.
- *Shape of base.*—Rounded to slightly attenuate.
- *Texture.*—Rugose.
- *Pubescence.*—Very dense rugose hairs, light grayish-white, less than 0.1 mm long on underside of main vein.
- *Margin type.*—Crenate.
- *Color.*—Young and Mature leaves: Upper surface: 146 A. Lower surface: close to 191 A.
- *Petioles.*—Length: 2 cm on average for lower leaves; 1 cm or less on average for other leaves. Diameter: 2 mm. Color: 147 C.
- *Veins.*—Pattern: Pinnate. Color: Upper surface: close to 147 C. Lower surface: 147 C.

Durability: Highly durable to stresses; when crushed, foliage spreads typical sage odor.

Response time to flower: About 10 months when grown in the containers.

FLOWER

Natural flowering season: Continuous from June into July with some rebloom in September.

Inflorescence type and habit: Branched rarely or lightly, terminal verticillaster, labiate, no fragrance, flower lasts about one week on plant, self-cleaning.

Rate of flower opening: About 25% of flowers open at once, all flowers open in about 4 weeks.

Number of flowers: About 156 per spike.

Inflorescence size:
- *Diameter.*—1.5-2 cm.
- *Height.*—15 cm.

Peduncle:
- *Length.*—17 cm.
- *Diameter.*—2 mm.
- *Color.*—Mostly green 145 A with parts close to 191 A.
- *Orientation.*—Upright with secondary peduncles at 30°.
- *Strength.*—Strong.

Corolla:
- *Petal arrangement.*—Labiate with one upper lip and one 3-lobed lower lips having one main lobe and two smaller side lobes.
- *Size.*—11 mm long; 10 mm wide.
- *Margin.*—Entire upper lip; 3-lobed lower lip.
- *Tip shape.*—Emarginate upper lip; rounded lower lip.
- *Length.*—Average upper lip: 3 mm; average lower lip: 2 mm.
- *Width.*—Average upper lip: 1 mm; average lower lip: 3+ mm.
- *Petal quantity.*—2, fused at base.
- *Petal apex shape.*—Upper lip; broad elliptic; folded; lower lip spathulate.
- *Texture.*—Numerous bristly glandular hairs on outside of upper lip, same color as upper lip, less than 0.1 mm long.
- *Aspect.*—Drooping.
- *Petaloids.*—None.

Color:
- *Upper lip.*—When opening: Upper surface: N78 C. Lower surface: N78 C. Fully opened: Lower surface: base is near white.
- *Petals.*—When opening: Upper surface: N78 A. Lower surface: N78 A. Fully opened Lower surface is near white.

Bud:
- *Shape.*—Obovate.
- *Length.*—4 mm.
- *Diameter.*—2 mm.
- *Color.*—N77 A.

Calyx:
- *Arrangement.*—5 sepals fused into a tube at 60% of the length; 3 upper sepals fused nearly at the tips; 2 lower sepals fused nearly at the tips.
- *Height.*—7 mm.
- *Diameter.*—4 mm.
- *Shape.*—Tubular.
- *Sepals.*—Shape: Elliptic with acute tip and crenate base. Size: Average 5 mm long; 1 mm wide. Margin: Entire. Texture: Grayish hairs; less than 0.2 mm long. Color: Outer surface: N79 B at the top half. Inner surface: from the tips down N79 B. Bracts: 2 bracts 6 mm width and 8 mm length under each whorl of flowers; deltoid shape with apiculate tip; upper surface 77 A lower surface 77 A.
- *Odor.*—Present in petals and sepals, scent same as foliage.

REPRODUCTIVE ORGANS

Stamens:
- *Number.*—2.
- *Filament length.*—5 mm.
- *Anthers.*—Shape: Basifixed, elliptic. Length: 1 mm. Color: whitish.
- *Pollen.*—Color: white; too little to determine color. Amount: Very low.

Pistil:
- *Number.*—One.
- *Length.*—12 mm.
- *Style.*—Length: 12 mm. Color: N78 A,B & C at the top half fading to white at the base.
- *Stigma.*—Shape: Cleft (2 parted). Color: N77 A. Ovary color: initially green close to 139 D.

Seeds and fruits: Yes brown and round 1.5 mm long and 1 mm wide, color 200 B.

Disease/pest resistance: No unusual susceptibility to diseases or pests has been noted to date.

Temperature tolerance: Tolerate to heat at least up to 30° C. and cool at least down to USDA Zone 5.

I claim:

1. A new, distinct *Salvia nemorosa* plant as shown and described, characterized by the combination of purple stems, deep pink flowers, and purple calyxes compared to the seed parent.

* * * * *